United States Patent [19]
Tanaka et al.

[11] Patent Number: 5,432,601
[45] Date of Patent: Jul. 11, 1995

[54] FINE PARTICLE ANALYZING DEVICE

[75] Inventors: Hiroshi Tanaka; Masashi Ohmori, both of Itami, Japan

[73] Assignee: Mitsubishi Denki Kabushiki Kaisha, Tokyo, Japan

[21] Appl. No.: 167,086

[22] Filed: Dec. 16, 1993

[30] Foreign Application Priority Data

Dec. 17, 1992 [JP]  Japan .................. 4-337229

[51] Int. Cl.⁶ .............................................. G01N 1/10
[52] U.S. Cl. ...................... 356/246; 356/336; 356/339; 356/342; 356/343; 250/574
[58] Field of Search .............. 356/339, 336, 335, 337, 356/338, 340, 341, 342, 343, 246; 250/574

[56] References Cited

U.S. PATENT DOCUMENTS

| | | | |
|---|---|---|---|
| 3,177,760 | 4/1965 | Albert | 250/574 |
| 4,066,904 | 1/1978 | Bertaux et al. | 250/372 |
| 4,067,653 | 1/1978 | Fletcher et al. | 356/246 |
| 4,068,125 | 1/1978 | Bell | 356/318 |
| 4,212,539 | 7/1980 | Berber et al. | 356/339 |
| 4,591,268 | 5/1986 | Lew | 356/246 |
| 5,030,843 | 7/1991 | Wakamura | 356/339 |
| 5,155,543 | 10/1992 | Hirako | 356/343 |

FOREIGN PATENT DOCUMENTS

63-63944  3/1988 Japan .
2190744  7/1990 Japan .

Primary Examiner—Richard A. Rosenberger
Assistant Examiner—Jason D. Eisenberg
Attorney, Agent, or Firm—Leydig, Voit & Mayer

[57] ABSTRACT

A device for analyzing fine particles in a sample gas includes a light source for emitting light, a convergent device for converting the light emitted by the light source into a convergent light beam having a light focus point and an energy density sufficient to dissociate the fine particles to be analyzed. The device also includes a transparent analyzer tube having a window for admitting the convergent light beam and a throat located at the light focus point of the convergent light beam, the analyzer tube receiving the sample gas and passing the sample gas through the throat. The device includes a light collecting device for collecting, through the analyzer tube, light emitted from dissociated fine particles, dissociated by the convergent light beam in the throat of the analyzer tube, and an analyzing device for analyzing the light from the dissociated fine particles collected by the collecting device.

4 Claims, 5 Drawing Sheets

FINE PARTICLE ANALYZING DEVICE

BACKGROUND OF THE INVENTION

This invention relates to a fine particle analyzing device and, more particularly, to a fine particle analyzing device suitable for analyzing a fine particle in a low-pressure sample gas which is, for example, in a process chamber in a semiconductor manufacturing process.

Figure 5:
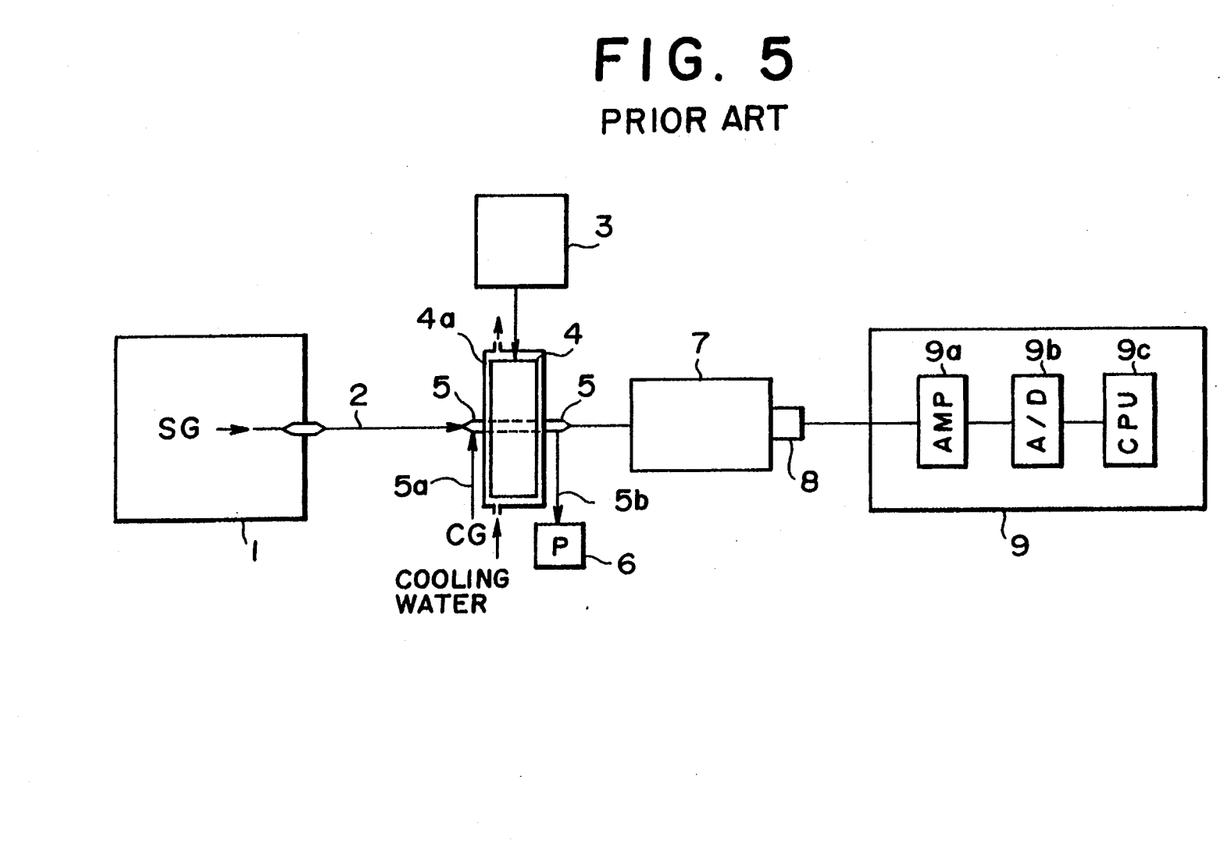
FIG. 5 is schematic diagram of a known fine particle analyzing device.

FIG. 5 is a diagram of a known fine particle analyzing device disclosed in Japanese Patent Laid-Open No. 2-190744. In FIG. 5, a introduction tube 2 is inserted at one end of a chamber 1 filled with a sample gas (SG), in which fine particles to be analyzed may be included, for introducing the sample gas from the chamber 1. Also, the tube 2 is connected at the other end to an analyzer tube 5 made of quartz. The analyzer tube 5 extends through a cavity 4 over the entire length of the cavity 4. A microwave source 3 is disposed for emitting a microwaves into the cavity 4. Connected to the other end of the analyzer tube 5 is a spectroscope 7 for analyzing the fine particles in the sample gas qualitatively and quantitatively. The cavity 4 is a thin can-shaped member filled with a cooling medium of a suitable fluid such as dry air. Also, a cooling means 4a such as a pipe for supplying a coolant is disposed along the entire circumference of the cavity 4. A photoelectric transducer 8 is electrically connected to the spectroscope 7 in the side opposite to the analyzer tube 5 and a signal processing device 9 is electrically connected to the photoelectric transducer 8. The signal processing device 9 comprises an amplifier 9a, an analog-to-digital (A/D) converter 9b and a central processing unit (CPU) 9c.

Perpendicularly disposed to the side wall of the analyzer tube 5 are a carrier-gas intake pipe 5a connected thereto near the introduction tube 2 for introducing a carrier gas CG such as argon or helium into the analyzer tube 5 and a gas exhaust pipe 5b connected near the other end of analyzer tube 5. An exhaust pump 6 is connected to the end of the gas exhaust pipe 5b. A gas in the analyzer tube 5 is exhausted through the gas exhaust pipe 5b by the exhaust pump 6.

In the known fine particle analyzing device as described above, the sample gas SG is introduced from the chamber 1 to the analyzer tube 5 through the capillary tube 2. In the analyzer tube 5, the sample gas SG is mixed with the carrier gas CG such as argon or helium introduced through the carrier-gas intake pipe 5a. Microwave power is applied through the cavity 4 to the mixed gas in the analyzer tube 5 so that a plasma of the mixed gas is generated in the analyzer tube 5. When the plasma is generated, the fine particles in the sample gas SG are dissociated and ionized by the plasma. The ionized fine particles, the sample gas SG and the carrier gas CG respectively emit light with characteristic spectra. Further, these gases are exhausted from the analyzer tube 5 through the gas exhaust pipe 5b and the exhaust pump 6.

The light generated in the analyzer tube 5 is separated into spectral components by the spectroscope 7. Only the separated spectral components having a wavelength within a wavelength range which may be considered to be generated by the ionized fine particles are selected and converted into electric signals, indicating light intensities, in the photoelectric transducer 8. The electric signals are amplified by the amplifier 9a of the signal processing device 9 and converted into light intensity digital signals by the analog-to-digital (A/D) converter 9b. The light intensity digital signals are determined qualitatively on the basis of the wavelengths of the spectral components by the central processing unit (CPU) 9c. Since the sample gas SG is continuously introduced from the chamber 1 into the analyzer tube 5 and exhausted therefrom, the change of the light intensities of the spectral components generated from the fine particles in the sample gas SG in accordance with the lapse of time becomes pulse signals corresponding to each of the fine particles. Therefore, by counting the number of the peaks of the pulse signals, the number of the fine particles can be determined.

In the known fine particle analyzing device as described above, since energy for dissociating the fine particles to be ionized is generated by collisions between the ions and the electrons which have a high kinetic energy in the plasma, when the kinetic energies of the ions and the electrons are low, the fine particles often cannot be dissociated. Based on our original study, if a plasma is to be generated in a suitable known method such as the ECR method or the multipolar magnetic field method in which a plasma for dissociating the fine particles can be generated by the lowest energy in the current art, the plasma cannot be generated at a pressure below, atmost several Torrs (1 Torr is one-760th of one atmosphere.)

However, in most of the process chambers for use in a semiconductor manufacturing process, since the pressure therein for depositing a film or etching a surface of a semiconductor wafer may be low, such as from several mTorr to several ten mTorr. When a process gas including fine particles which are particularly considered to be a cause of the failure of semiconductor devices in the process chamber is directly introduced as the sample gas SG into the known fine particle analyzing device described above as the sample gas SG, since the pressure in the process chamber is much lower than the pressure necessary for dissociating the fine particles, the fine particles cannot be dissociated at all.

Further, sizes of the fine particles vary for example, there are large particles undesirably attaching to a wafer surface to become a direct cause of a conductor breaking or an electrical short-circuit, medium particles resulting in a poor reliability such as from one-third to one-fifth of a width of the conductor pattern and very small particles as failure nuclei. Therefore, the causes of failure are based on the sizes of the fine particles, and information concerning the sizes of the fine particles is very important. However, since it is difficult to gain the information concerning the sizes in the known fine particle analyzing device as described above, it has been estimated from the qualitative analysis. As the spectral components having a wavelength in a wavelength range which may be considered to be generated from the ionized fine particles only are selected by the photoelectric transducer 8, the estimation becomes ineffectual if a fine particle is almost composed of other components. Then, a dust counter and a wafer surface checking device are necessary to obtain information concerning sizes of the fine particles. Further, the sizes of the fine particles need to be estimated statistically from the qualitative data and size data from the dust counter and the wafer surface checking device.

Also, as the analyzer tube 5 is heated by the plasma to more than 2,000° C. and the quartz composing the analyzer tube 5 may be melted, a cooling means 4a as described above should be provided to the analyzer tube 5 for cooling the analyzer tube 5 and it is not easy to cool the analyzer tube 5.

SUMMARY OF THE INVENTION

Accordingly, one object of the present invention is to provide a fine particle analyzing device free from the above-discussed problems of the known fine particle analyzing device.

Another object of the present invention is to provide a fine particle analyzing device in which a sample gas whose pressure is as low as from several mTorr to several ten mTorr is directly introduced and fine particles in the sample gas can be efficiently dissociated and ionized.

Another object of the present invention is to provide a fine particle analyzing device in which sizes of fine particles in a sample gas can be determined at the same time that number of the fine particles is counted and the fine particles are analyzed qualitatively.

Still another object of the present invention is to provide a fine particle analyzing device in which a size of each fine particle can be easily put into correspondence with its quantity.

A futher object of the present invention is to provide a fine particle analyzing device in which an analyzer tube can be cooled easily.

With the above objects in view, the fine particle analyzing device of the present invention comprises a light source for emitting light, convergent means for converting the light emitted from the light source into a convergent light beam having, at a light focus point, an energy density sufficient to dissociate the fine particles to be analyzed, a transparent analyzer tube having a window for admitting the convergent light beam therein and an inner surface configuration having a throat portion corresponding to the light focus point of the convergent light beam, the analyzer tube introducing the sample gas therein and passing the sample gas through the throat portion thereof, exhausting means connected to the analyzer tube for exhausting the sample gas in the analyzer tube, light collecting means for collecting, through the analyzer tube, dissociation light emitted from the fine particles dissociated by the convergent light beam in the throat portion of the analyzer tube and analyzing means connected to the collecting means for analyzing the dissociation light collected by the collecting means.

The fine particle analyzing device of the present invention further comprises optical stop means for adjusting luminous intensity of the light emitted from the light source, convergent angle adjusting means for adjusting the convergent angle of the convergent light beam converged by the convergent means, collecting position adjusting means for adjusting a position of the light collecting means with respect to the analyzer tube and gas introducing speed controlling means for controlling sample gas introducing speed.

The present invention also resides in a method for analyzing a sample gas and fine particles therein, the method comprising the steps of generating a convergent light beam having an energy density sufficient to dissociate the fine particles to be analyzed at a light focus point thereof, introducing the sample gas into the light focus point of the convergent light beam and illuminating the sample gas with the convergent light beam, whereby dissociation light is emitted from the fine particles, and analyzing the dissociation light to analyze the fine particles.

BRIEF DESCRIPTION OF THE DRAWINGS

The present invention will become more readily apparent from the following detailed description of the preferred embodiments of the present invention taken in conjunction with the accompanying drawings, in which.

DESCRIPTION OF THE PREFERRED EMBODIMENTS

Figure 1:
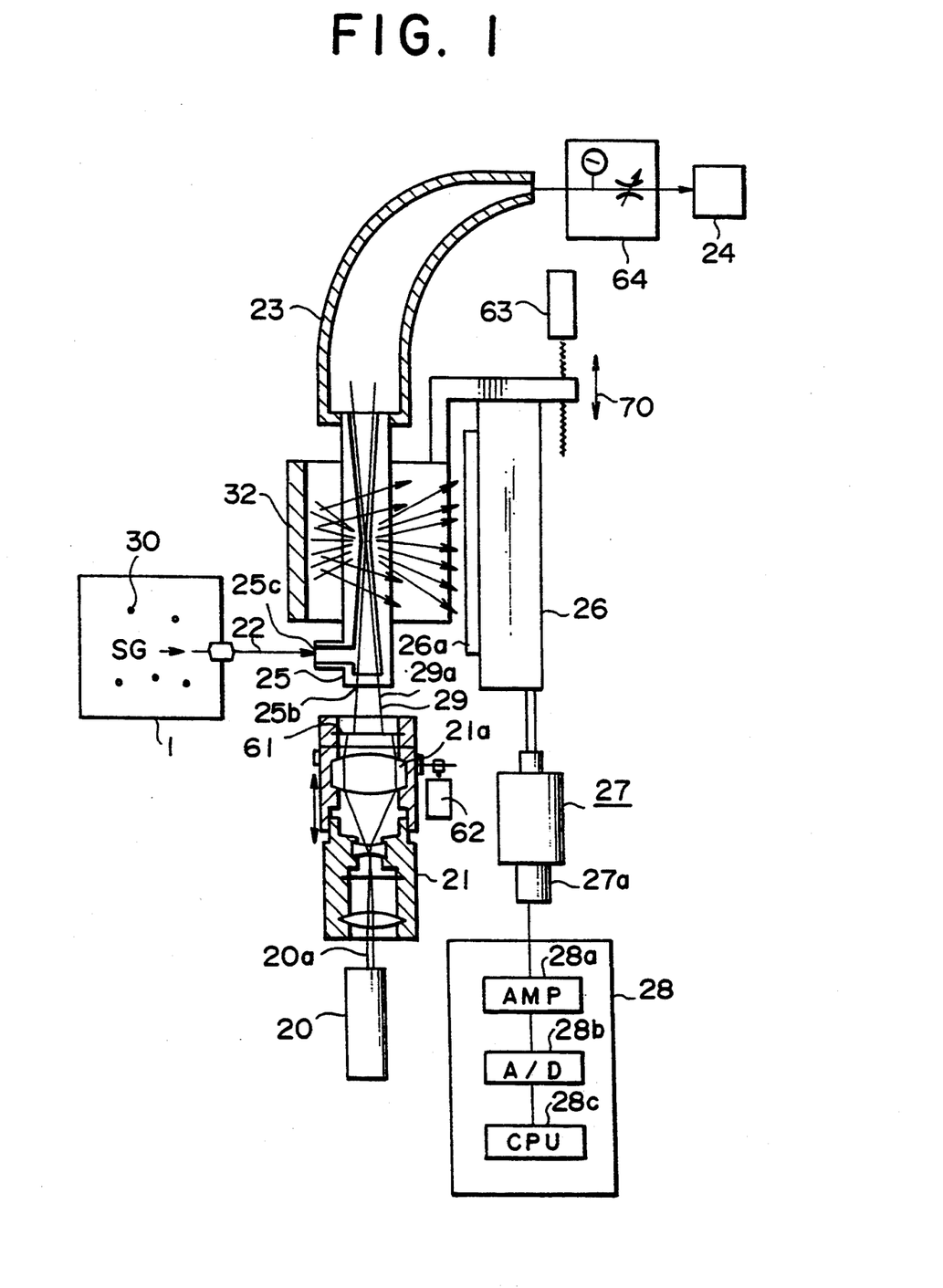
FIG. 1 is a schematic diagram of a fine particle analyzing device of the present invention.

FIG. 1 illustrates an embodiment of a fine particle analyzing device of the present invention, which comprises a light source 20 for emitting a light 20a and convergent means 21 for converting the light 20a emitted from the light source 20 into a convergent light beam 29. A sample gas SG is introduced into a transparent analyzer tube 25 disposed in the light path 29a of the convergent light beam 29. The analyzer tube 25 has a window 25b for introducing the light beam 29 therein and illuminating the sample gas SG in the analyzer tube 25. For the light source 20, a light source emitting light having a wavelength from about ultraviolet light to visible light such as a UV (ultraviolet) lamp and a laser oscillator is used. When the UV lamp is used as the light source 20, a compound lens is disposed in the convergent means 21 for correcting an aberration of the convergent light beam 29. On the other hand, when a laser oscillator is used, a beam expander is disposed in the convergent means 21.

Further, a gas introducing tube 22 is connected at its one end to a chamber 1 filled with the sample gas SG, in which fine particles to be analyzed may be included, for introducing the sample gas SG from the chamber 1 therein. Also, the gas introducing tube 22 is connected at the other end to a sample gas inlet hole 25c provided in the side portion of the analyzer tube 25. The analyzer tube 25 is a silica tube having a high light-transmittance with respect to ultraviolet light to visible light.

Figure 2:
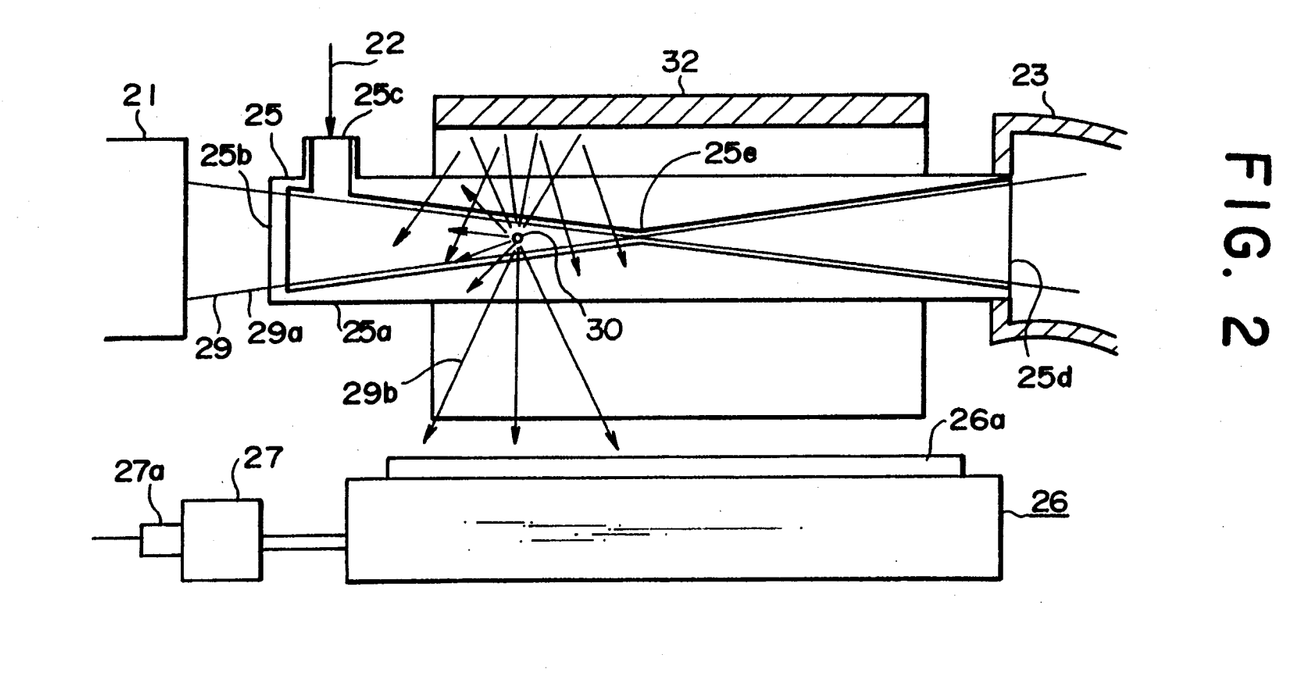
FIG. 2 is an enlarged sectional view of the analyzer tube illustrated in FIG. 1.

FIG. 2 is an enlarged view of the analyzer tube 25. As illustrated in FIG. 2, the light admitting window 25b and a gas exhaust port 25d are provided at opposite ends of the main body 25a of the analyzer tube 25 respectively, and the sample gas inlet hole 25c is provided in the side wall portion of the main body 25a. As for the inner surface configuration of the main body 25a of the analyzer tube 25, it is a pair of the conical bores connected to each other at their tips and a throat portion 25e provided at the middle portion thereof, which is the connecting portion between the two conical bores, corresponding to the light focus point of the convergent light beam 29 converged by the convergent means 21. The throat portion 25e has an inner diameter smaller than that of the light admitting window 25b. Hence, the inner surface configuration of the analyzer tube 25 corresponds to the contour of the convergent light beam 29 so that it does not shield or intercept the light path 29a of the light beam 29 and the fine particles 30 in the sample gas SG are prevented from moving outside of the light path 29a. As illustrated in FIG. 1, a gas exhaust pipe 23 and a gas exhaust pump 24 are connected to the gas exhaust port 25d of the analyzer tube 25. The sample gas SG is introduced into the analyzer tube 25 by the exhaust pump 24.

Figure 3:
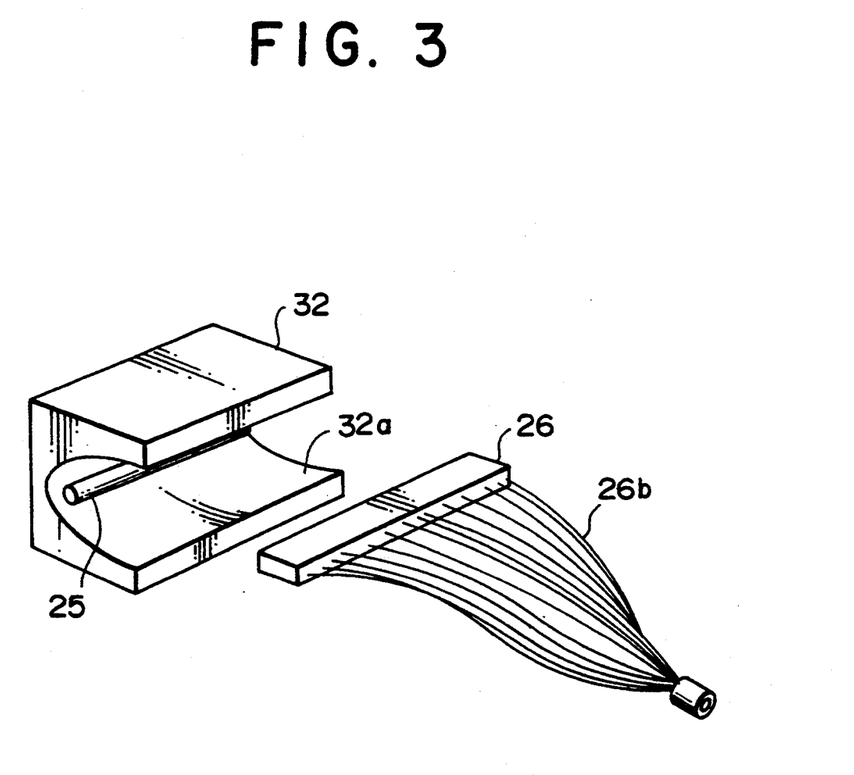
FIG. 3 is a perspective view of the light collecting mirror and the light collecting device illustrated in FIG. 1.

Further, a light collecting mirror 32 is disposed such that it surrounds the analyzer tube 25 and a light collecting device 26 is disposed opposite to the light collecting mirror 32. The light collecting device 26 has a light receiving surface 26a having for example, a cylindrical lens (not shown) for collecting light emitted from the fine particles 30. As for the light collecting mirror 32, a cylindrical mirror for example may be used. FIG. 3 shows the light collecting mirror 32 and the light collecting device 26. As illustrated in FIG. 3, the light collecting mirror 32 has a bore 32a therein open to the outside at its side wall parallel to the light receiving surface 26a of the light collecting device 26. The bore 32a has a half-elliptic shaped cross section. The light collecting device 26 comprises a plurality of light collecting fibers 26b made, for example, of quartz and having a high transmittance with respect to a light from ultraviolet light to visible light. Also, as illustrated in FIG. 1, a spectroscope 27 is electrically connected to the end of the light collecting device 26 and a photoelectric transducer 27a is electrically connected to the spectroscope 27. As for the spectroscope 27, a monochromator in which the spectroscope 27a is mounted may be used. Further, a signal processing device 28 is electrically connected to the spectroscope 27. The signal processing device 28 comprises an amplifier 28a, an analog-to-digital (A/D) converter 28b and a central processing unit (CPU) 28c mounted therein.

The sample gas SG and the fine particles 30 in the sample gas SG are various. For example, as for the sample gas SG, there is air, an inactive gas such as $N_2$ and Ar and a corrosive gas such as $Cl_2$. On the other hand, as for the fine particles 30, they are almost metallic ones and organic ones which exist in various conditions so that they mingle with each other or they are compounds of each other. Further, their sizes are diverse and different. Since the various fine particles 30 in the various sample gases SG as described above should be analyzed, it is necessary to set up a best and most efficient condition for the analysis with respect to each of the various fine particles and the various sample gases.

Then, in the fine particle analyzing device, as illustrated in FIG. 1, optical stop means 61 and convergent angle adjusting means 62 are disposed in the convergent means 21. The optical stop means 61 is disposed in the path of the light 20a for partially shielding or intercepting light to adjust the luminous intensity of the light 20a emitted from the light source 20. The convergent angle adjusting means 62 is disposed in the convergent means 21 for adjusting the position of the convergent lens 21a with respect to the analyzer tube 25 so as to adjust a convergent angle of the convergent light beam 29a. Also, collecting position adjusting means 63 is connected to the light collecting mirror 32 and the light collecting device 26 for moving them with respect to the analyzer tube 25 in the direction shown by an arrow 70 so as to adjust the position of the light focus point of the convergent light beam 29a. Further, disposed between the gas exhaust pipe 23 and the gas exhaust pump 24 is gas introducing speed controlling means 64 such as a mass flow controller for controlling the speed of introducing the sample gas SG from the chamber 1 into the analyzer tube 25 through the introducing tube 22 by the gas exhaust pump 24.

In the fine particle analyzing device of the present invention as described above, the sample gas SG including the fine particles 30 to be analyzed is introduced from the chamber 1 into the analyzer tube 25 through the introducing tube 22. The sample gas SG is illuminated by the convergent light beam 29 converged by the convergent means 21 in the analyzer tube 25. The energy density of the convergent light beam 29 continuously increases toward the light focus point and becomes highest at the light focus point at which the throat portion 25a of the analyzer tube 25 has the smallest inner diameter. Since the fine particles 30 are not dissociated between the light leading window 25b and the throat portion 25e of the analyzer tube 25, scattered light 29b is emitted from the fine particles 30 illuminated by the convergent light beam 29. As the fine particles 30 are illuminated at the throat portion 25e by the focused light beam 29 having the highest energy density sufficient to dissociate the fine particles 30, the fine particles 30 are dissociated and ionized and then dissociation light is emitted by the ionized fine particles 30 in the analyzer tube 25. Thereafter, these gases are exhausted through the gas exhaust pipe 23 and the gas exhaust pump 24 from the analyzer tube 25.

Since the light 20a emitted from the light source 20 is converted into the convergent light beam 29 by the convergent means 21 so that the energy density of the light beam 29 continuously increases, and further, the fine particles 30 are illuminated within a small space, the light 20a does not need to be strong. Therefore, the analyzer tube 25 is heated only in the vicinity of the throat portion 25e of the analyzer tube 25 in which the convergent light beam 29 has the highest energy density. The analyzer tube 25 is not so heated as a whole and the cooling means 4a as illustrated in FIG. 5 is not needed for cooling the analyzer tube 25. If necessary, dry air may be simply supplied such that it surrounds only the vicinity of the throat portion 25e for dissipating heat. Further, the external shape of the analyzer tube 25 may, if necessary, be formed along the inner surface configuration thereof so that wall thickness of the analyzer tube 25 becomes uniform as a whole for achieving efficient heat dissipation.

The scattered light 29b (See FIG. 2) emitted from the fine particles 30 before the dissociation is collected at the light receiving surface 26a of the light collecting device 26 disposed opposite the light collecting mirror 32 by the light collecting mirror 32 disposed opposite to the analyzer tube 25. The collected light is led to the spectroscope 27 through the light collecting fibers 26b and separated into spectral components by the spectroscope 27 in which only a characteristic wavelength area of the scattered light 29b is selected. Here, the characteristic wavelength of the scattered lights 29b corresponds to the characteristic wavelength of the light 20a emitted from the light source 20. Therefore, when the light source 20 is an UV lamp, a wavelength area having a comparatively long wave-length from ultraviolet light to visible light, except for light considered to be generated from the components composing the fine particles 30, is selected. On the other hand, when the light source 20 is a laser oscillator, the wave-length of the laser beam emitted from the laser oscillator is selected.

Further, the separated scattered light 29b separated by the spectroscope 27 is converted into electric signals, indicating light intensities, by the photoelectric transducer 27a. The electric signals are amplified by the amplifier 28a of the signal processing device 28 and converted into light intensity digital signals by the analog-to-digital (A/D) converter 28b. The light intensity digital signals are processed by the central processing unit (CPU) 28c to determine the number and the sizes of the fine particles 30 in the sample gas SG. Also, at the same time, the dissociation light emitted from the ionized fine particles 30 is collected by the light collecting mirror 32 and the light collecting device 26 and separated by the spectroscope 27. The components composing the ionized fine particles 30 are selected and analyzed by the photoelectric transducer 27a and the signal processing device 28 to determine the components of the fine particles 30 on the basis of the wavelengths of the separated spectral components.

Figure 4:
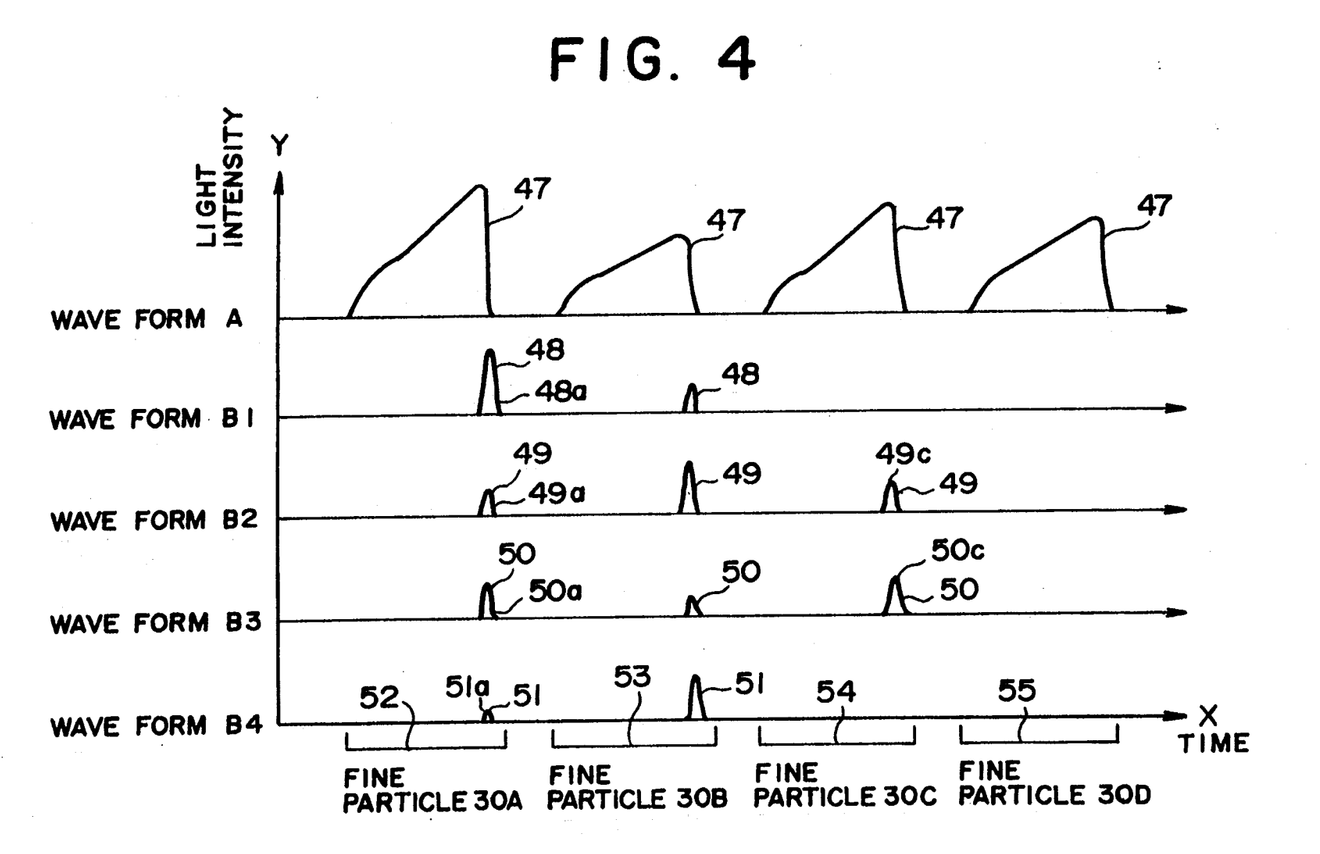
FIG. 4 is a graph indicating information concerning quality and size of each analyzed fine particle and the number of the fine particles.

FIG. 4 is a graph showing information concerning each analyzed fine particle 30. In FIG. 4, the X-axis represents time and the Y-axis represents light intensity. Pulse signals 47 of a waveform A are light intensity signals due to the scattered light 29b reflected from the fine particles 30. Pulse signals 48 of a waveform B1, pulse signals 49 of a waveform B2, pulse signals 50 of a wave form B3 and pulse signals 51 of a waveform B4 respectively are light intensity signals generated by the spectral components of the dissociated and ionized fine particles 30 and each of the waveforms is set up at a different wavelength. In FIG. 4, fine particles 30A, 30B, 30C and 30D, which are shown by numerals 52, 53, 54 and 55, correspond to the fine particles 30. For example, the fine particles 30A are composed of four components indicated by four pulse signals 48a, 49a 50a and 51a of each waveform B1~B4. The fine particles 30B are composed of the same four components as the fine particles 30A, however, in a different ratio. The fine particles 30C are composed of two components, which are indicated by two pulse signals 49c and 50c of the waveform B2 and B4, and other components. The fine particles 30D are composed of other components those that correspond to the waveform B1~B4. Thus, the components of each of the fine particles 30 can be determined qualitatively.

A method for determining the number and the sizes of each of the fine particles 30 is as follows. As described above, when the fine particles 30 are illuminated by the light beam 29 before they are dissociated, the scattered light 29b (See FIG. 2) is generated. Further, since the sample gas SG is continuously introduced into the analyzer tube 25 from the chamber 1 by the gas exhaust pump 24 and exhausted, the change of the light intensity has a saw-teeth shape such as the pulse signals 47 of the waveform A. And each of the pulse signals 47 corresponds to the each of the fine particles 30 respectively. Therefore, the number of the fine particles 30 can be detected by counting the peaks of each of the pulse signals 47 with time. Also, as for the sizes of the fine particles 30, it also is indicated by the waveform A, because the sizes of the fine particles 30 are the values of the light intensities shown by each of the peaks of the pulse signals 47 of the waveform A generated by the scattered light 29b.

According to the fine particle analyzing device of the present invention, the fine particles 30 including the fine particles 30C (See FIG. 4), which cannot even be estimated by the known fine particles analyzing device illustrated in FIG. 5, can be analyzed so that information concerning the size of each of the fine particles 30 can be put into precise correspondence with the qualitative information thereon.

Further, in the fine particle analyzing device of the present invention, the luminous intensity of the light 20a emitted from the light source 20 can be adjusted with the optical stop means 61, the convergent angle of the convergent light beam 29a can be adjusted by the convergent angle adjusting means 62 and the position of the light collecting mirror 32 and the light collecting fibers 26b can be moved with respect to the analyzer tube 25, and the speed of introducing the sample gas SG into the analyzer tube 25 can be controlled with the gas introducing speed controlling means 64. The energy of the light beam 29 can efficiently dissociate and ionize the fine particles 30 considering the degree of an interference of the sample gas SG in the dissociation of the fine particles 30.

In the fine particle analyzing device of the present invention, as described above, since a light beam is used, instead of a plasma, to dissociate the fine particles by illuminating them directly, the fine particles 30 in the sample gas even at a low pressure can be dissociated stably, irrespective of the pressure of the sample gas.

Further, since the light beam 29 is gradually converged so that the energy density of the light beam 29 continuously increases, the power of the light 20a emitted from the light source 20 can be lower. As the fine particles 30 are not dissociated between the light admitting window 25b and the throat portion 25e of the analyzer tube 25, the number and the sizes of the fine particles 30 can be determined from the scattered light 29b emitted from the fine particles 30 before they are dissociated. As the fine particles 30 are dissociated and analyzed qualitatively, information on the sizes of each of the fine particles 30 can be easily put into correspondence with the qualitative information thereof.

Since the analyzer tube 25 has the above-described inner surface configuration comprising a throat portion 25e having a diameter smaller than that of the light admitting window 25b, the fine particles 30 are always within the path 29a of the light beam 29. Then, the fine particles can be dissociated efficiently. Thus, there is almost no fine particle which cannot be dissociated and analyzed and exhausted.

As the convergent light beam 29 has an energy density sufficient to dissociate the fine particles 30 only at the vicinity of the light focus point, the temperature of the analyzer tube 25 does not become high as a whole. Only the vicinity of the light focus point may need to be cooled and heat dissipation of the analyzer tube 25 becomes more efficient and much easier than that in the known analyzing device illustrated in FIG. 5.

What is claimed is:

1. A fine particle analyzing device for analyzing fine particles in a sample gas comprising:
   a light source for emitting light;
   convergent means for converting the light emitted by said light source into a convergent light beam having a light focus point and an energy density sufficient to dissociate fine particles to be analyzed;
   a transparent analyzer tube having a light admitting window for admitting the convergent light beam, a length, and a throat centrally located along the length of said analyzer tube at the light focus point of the convergent light beam, said analyzer tube receiving the sample gas and passing the sample gas through said throat;

exhausting means connected to said analyzer tube for exhausting the sample gas from said analyzer tube;

light collecting means for collecting light scattered from fine particles in said analyzer tube and light emitted by fine particles dissociated by the convergent light beam in said throat of said analyzer tube, said light collecting means including a mirror disposed along the length of and partially surrounding said analyzer tube and a longitudinal array of optical fibers disposed along the length of and opposite said analyzer tube and said mirror for transmitting light scattered and emitted at respective positions along the length of said analyzer tube; and analyzing means connected to said light collecting means for analyzing the light scattered by the fine particles and emitted by dissociated fine particles and collected by said collecting means.

2. The fine particle analyzing device as claimed in claim 1 comprising:

optical stop means for adjusting luminous intensity of the light emitted by said light source and incident on said light admitting window;

convergent angle adjusting means for adjusting a convergent angle of the convergent light beam converged by said convergent means;

collecting position adjusting means for adjusting a position of said light collecting means with respect to said analyzer tube; and gas introducing speed controlling means for controlling introduction of the sample gas into said analyzer tube.

3. The fine particle analyzing device as claimed in claim 1 wherein the energy density of the convergent light beam continuously increases toward the light focus point.

4. The fine particle analyzing device as claimed in claim 1 wherein said transparent analyzer tube comprises a first conically shaped interior surface converging towards said throat and a second conically shaped interior surface converging towards said throat, said first and second conically shaped interior surfaces being connected at said throat.

* * * * *